US008399106B2

(12) United States Patent
Kukkonen et al.

(10) Patent No.: US 8,399,106 B2
(45) Date of Patent: Mar. 19, 2013

(54) COMPOSITION AND METHOD FOR TREATING WOOD

(75) Inventors: Jari-Jukka Kukkonen, Oulu (FI); Timo Nissinen, Ylöjärvi (FI); Aksela Reijo, Espoo (FI)

(73) Assignee: Kemira OyJ, Helsinki (FI)

( * ) Notice: Subject to any disclaimer, the term of this patent is extended or adjusted under 35 U.S.C. 154(b) by 229 days.

(21) Appl. No.: 12/745,584

(22) PCT Filed: Dec. 3, 2008

(86) PCT No.: PCT/FI2008/050707
§ 371 (c)(1),
(2), (4) Date: Jul. 29, 2010

(87) PCT Pub. No.: WO2009/071745
PCT Pub. Date: Jun. 11, 2009

(65) Prior Publication Data
US 2010/0297460 A1 Nov. 25, 2010

(30) Foreign Application Priority Data
Dec. 3, 2007 (FI) ..................... 20070935

(51) Int. Cl.
*B32B 21/04* (2006.01)
(52) U.S. Cl. .................. 428/537.1; 427/384; 427/393
(58) Field of Classification Search ............... 428/537.1; 427/384, 393
See application file for complete search history.

(56) References Cited

U.S. PATENT DOCUMENTS

| | | | |
|---|---|---|---|
| 4,179,522 A | 12/1979 | Huitson | |
| 4,643,754 A | 2/1987 | Nance | |
| 4,808,407 A | 2/1989 | Hein et al. | |
| 4,871,473 A | 10/1989 | Goettsche et al. | |
| 5,051,283 A * | 9/1991 | Beane et al. | 427/440 |
| 5,276,029 A | 1/1994 | Goettsche et al. | |
| 5,444,093 A | 8/1995 | Goettsche et al. | |
| 5,582,871 A | 12/1996 | Silenius et al. | |
| 6,211,218 B1 | 4/2001 | Goettsche et al. | |
| 6,352,583 B1 | 3/2002 | Goettsche et al. | |
| 6,652,921 B2 | 11/2003 | Raczek et al. | |
| 2006/0148313 A1 | 7/2006 | Lantto et al. | |

FOREIGN PATENT DOCUMENTS

| | | |
|---|---|---|
| EP | 0320786 B1 | 6/1989 |
| EP | 0682091 | 11/1995 |
| EP | 0641275 | 6/1997 |
| EP | 1070045 | 2/2004 |
| EP | 1361938 | 11/2004 |
| FI | 117792 B | 2/2007 |
| JP | 1-202-404 | 8/1989 |
| JP | 08-291007 | 11/1996 |
| JP | 2001-150404 | 6/2001 |
| JP | 2001187401 A | 7/2001 |
| JP | 2001239506 | 9/2001 |
| JP | 2005329703 A | 12/2005 |
| WO | 9839146 | 9/1998 |
| WO | 0123154 | 4/2001 |
| WO | 03002318 A1 | 1/2003 |
| WO | 03088745 A1 | 10/2003 |
| WO | 2004/035718 A2 | 4/2004 |
| WO | 2006071659 A1 | 7/2006 |
| WO | 2006072659 A1 | 7/2006 |
| WO | 2006072672 A1 | 7/2006 |
| WO | WO2006/072659 * | 9/2006 |

OTHER PUBLICATIONS

Second Amended Statement of Case, dated Jun. 28, 2010 in the matter of New Zeland Patent Application FI567526; for Kemria Oyj; 18 pages.
English Abstract of NZ567526, located at http://v3.espacenet.com/publicationDetails/biblio?DB+EPODOC&adjacent+true&locale . . . , dated Nov. 11, 2010; 1 page.
Certified Translation of JP2001-150404 by Park IP Translations, dated Jul. 20, 2010, cover page, pp. 1-15.
Office Action from related Canadian Patent Application No. 2,708,180 prepared by Charles Barabe', Patent Examiner on Nov. 1, 2011.
International Search Report; International Application No. PCT/FI2008/050707; International Filing Date Dec. 3, 2008, 3 pages.
Written Opinion of the International Searching Authority; International Application No. PCT/FI2008/050707; International Filing Date Dec. 3, 2008; 4 pages.
English Abstract of JP2005329703A; entitled "Antiseptic and Termite Repellent of Timber and Treating Method of Timber Using It"; published Dec. 2, 2005; filed Nov. 16, 2004; 1 page.
English Abstract for JP08-291007; entitled "Wood Preservative Composition and Prevention of Discoloration of Wood During Is Treating Using the Same" published May 11, 1996; filed Apr. 19, 1995; 1 page.
English Abstract of EP 0320786(A1); entitled "Wood-protecting agent" pubished Jun. 21, 1989; 2 pages.
English Abstract of JP 01-202404 entitled "Wood Preservative"; published Aug. 15, 1989; filed Dec. 14, 1988, 1 page.
English Abstract for JP2001187401A; entitled "Antiseptic Wood-Preserving Agent" published Jul. 10, 2001; filed Dec. 28, 1999; 1 page.
English Abstract for JP2001-239506A; entitled Method for Protecting Wood and Wooden Product from Generation of Fungi; filed Jan. 24, 2001; published Sep. 4, 2001, 1 page.
English Translation of Japanese Office Action for Application No. 2008-110019; Mailing Date: Feb. 18, 2011, 7 pages.
Japanese Office Action for Application No. 2008-110019; Mailing Date: Feb. 18, 2011; 6 pages.

* cited by examiner

*Primary Examiner* — Leszek Kiliman
(74) *Attorney, Agent, or Firm* — Thomas Horstemeyer, LLP

(57) ABSTRACT

According to the invention, wood material is treated with a composition comprising at least one C1-C7 monocarboxylic acid or a salt, or mixtures thereof, and at least one chelating agent. These compounds are dissolved in a liquid aqueous vehicle. In this manner, the treated wood is endowed with excellent resistance against detrimental environmental effects.

17 Claims, No Drawings

COMPOSITION AND METHOD FOR TREATING WOOD

CROSS REFERENCE TO RELATED APPLICATIONS

This is a U.S. national stage of application No. PCT/FI2008/050707, filed on 3 Dec. 2008, the disclosure of which is incorporated herein by reference.

The invention relates to a composition and method for the treatment of wood, said composition and method mainly improving the durability of wood products but also other properties such as fire resistance. Moreover, the invention is directed to wood materials thus obtained.

In Europe, wood material is expensive and thus elevation of the degree of upgrading is widely considered as the only option in the field to assure growth or at least preservation of the present level of business. Prevention of biological decay of wood and improvement of the fire and water resistances thereof are known to be sectors where the upgrading value of wood should be particularly elevated. One of the significant obstacles for using wood as construction material is fire safety. On many markets, for instance in Japan, it would also be preferable for wood to retain its normal original colour as long as possible. Darkening of wood due to sunlight and humidity is considered to be architecturally esthetical, said darkening thus contributing to the reduction of the use of wood in the construction industry.

Microbes of wood are often divided into two groups according to the enzymatic activities and decomposition abilities thereof. The first group consists of fungi assimilating contents of dead plant cells without decomposing the lignified cell wall of wood cells. Said fungi include moulds and blue stain fungi. The other group consists of microbes utilizing lignified cell walls. Brown and white rot fungi are some of the most efficient decomposing fungi in this group, but also Actinobacteria and Ascomycetes fungi are able to decompose lignified cell wall of wood cells.

WO 03/002318 discloses the use of potassium formate and calcium formate in the form of aqueous solutions for the preservation of wood, particularly against rot fungi and termites. However, sufficient protection against rot, mould, or fire is not provided by this composition under demanding conditions.

FI 117792 discloses an agent for the treatment of wood, said agent comprising formate in combination with sorbate and/or benzoate, dissolved in a liquid aqueous vehicle. In comparison to WO 03/2002318, an advantage of this agent is the fact that it allows for the improvement of mould and fire resistances of wood. However, this fire resistance is not enough to satisfy the latest fire standards for wooden construction materials. Also the protection against rot and mould is not sufficient for demanding applications or for long term use.

Use of different formate solutions for the treatment of porous materials such as wood is also known from WO 03/088745, the purpose of the treatment being the inhibition of growth of moulds and fungi from spores. However, protection against rot, mould and fire provided by said solutions is not sufficient.

U.S. Pat. No. 6,652,921 discloses a process for the pretreatment of wood with an organic acid, preferably with citric acid, fumaric acid, or lactic acid, formic acid being included as a less preferable choice. After this pretreatment, wood is dried and finally treated with sorbic acid or a salt thereof. Concentration of the organic acid in the pretreatment solution is preferably from 1.0 to 5.0% by weight. The purpose is to create a permanent "depot" of weakly soluble sorbic acid in the wood by absorbing sorbate such as potassium sorbate into wood pretreated with acid. The treatment steps may also be performed in reversed order, but also in this case, the treatment is characterized by drying between the steps. Since the treatment is based on the use of organic acids alone, a drawback thereof is the insufficient protection against rot, fire, and moulds. Moreover, also dilute solutions of organic acids are strong acids, pH of the solutions often being below 4, and accordingly, wood material thus treated may deteriorate with time due to acids breaking wood structure.

An impregnating agent is known from EP 1361938, said agent being based on a mixture of a special double salt of formic acid and potassium formate, or potassium diformate, with organic acids. Aqueous solutions of potassium formate are acidic as such, and accordingly, wood material treated with said impregnation agent may deteriorate with time due to acids breaking wood structure.

EP 0 641 275 B1 discloses a process and agent for the protection of wood against wood rot wherein wood material is treated with a wood protecting agent inhibiting the growth and spreading of fungi, said agent comprising at least one sequestering agent such as ethylenediaminetetraacetic acid (EDTA), ethylenediamine-di-(o-hydroxyphenyl acetic acid) (EDDHA), polyphosphate, or siderophore. At least some of the metals naturally present in wood, e.g. iron and manganese, essential for the growth of fungi, are bound by said sequestering agent. A drawback of the treatment is the insufficient mould inhibition, and the tendency of the sequestering agent to be washed out of the wood with time. A worldwide aim is for instance to reduce the use of the most common and efficient sequestering agent, EDTA, due to very slow biodegradion thereof.

WO 0123154 A1 attempts to reduce washing out of the sequestering agents by the addition of siloxan derivatives, or fluoroalkyl polymers to the wood protection agent.

It is found that the use of acids in the protection of wood, for instance in a manner known from U.S. Pat. No. 6,652,921 and EP 1361938, is associated with the drawback that acidic conditions have an unfavourable effect on the original structure of wood material with time.

A group of environmentally acceptable and efficient chelating agents having a structure of the following formula (I) are known from the previous patent document EP 1070045 of the same applicant

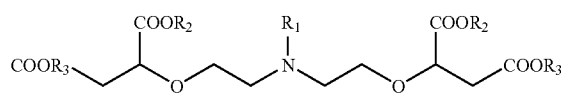

(1)

where $R_1$ is selected from a group consisting of alkyl groups, groups having a single carboxylic acid group in the alkyl chain, and $R_2$ and $R_3$ represent hydrogen, or alkali metal or alkaline earth metal ion. It is suggested to use these derivatives as chelating agents for the bleaching of chemical or mechanical pulp, or in bleaching agents for textiles containing hydrogen peroxide or peracid, or as an agent binding calcium in washing and detergent agents.

As is known, some carboxylic acids or sequestering agents (chelating agents) have inhibiting activities against the growth of rot fungi once wood is treated with aqueous solutions thereof. The advantage of some carboxylic acids or sequestering agents is the nontoxicity thereof in comparison to traditional CCA impregnation methods containing chromium, copper and/or arsene (copper chromium arsenate). However, carboxylic acids, or sequestering agents alone are not enough to provide the desired protection against rot, blue stain fungi, moulds, and fire. Also washing out thereof from the wood with time is considered to be a problem.

The object of the present invention is to provide a composition for the treatment of wood, characterized in that it
- is safe for the user and is only associated with a minor environmental hazard (not harmful),
- is well absorbed by, or penetrates well to all different types of wood materials, while remaining in wood without being washed out in significant amounts,
- protects wood against both moulds and rot and blue stain fungi,
- protects wood against dimensional changes, cracking and discolouration,
- improves fire resistance of wood,
- is not detrimental to the wood structure after treatment even in long term use.

Further, an object of the invention is to provide a wood product suitable for various different demanding application environments, said wood product simultaneously having several of the above preferable properties. A particular object of the invention is to provide a wood material simultaneously having superior rot resistance, superior fire resistance, and superior colour stability.

BRIEF DESCRIPTION OF THE INVENTION

To attain the objects of the invention, the composition for the treatment of wood is characterized as presented herein. Wood is treated as described herein, thus providing treated wood as described herein. Further, the invention discloses the use as described herein.

In the present invention, it was surprisingly found that rot and fire protection of wood may be significantly and simultaneously improved by the addition of both a formate salt and a chelating agent to the wood protection solution. Moreover, a significant synergy advantage is obtained in case wood is simultaneously protected against rot fungi, blue stain fungi, moulds, termites, fire, as well as discolouration. Such a versatile wood protecting agent only associated with a minor environmental hazard has not been so far commercially available notwithstanding the great need therefor.

Even though organic salts such as calcium formate are quite active against rot fungi (wood protection class 3; rot protection standard EN 350-1, classes 1-5), wood materials treated therewith belong, due to their short ignition time, in the most recent European fire classification system (fire protection standard EN 13501-1, classes A-D) to Class D, that is to the same class as completely untreated wood products. The wood protection solution now provided, or the composition for the treatment of wood comprising a formate salt in combination with a chelating agent, now enables the classification of treated wood material to class B, that is, to the best possible class for wood. Moreover, it was found that the composition based on formate and a chelating agent is able to convert wood to a form comparable to wood impregnated with CCA, that is, even the best wood protection class 1 is reached.

It was found that both the growth of moulds and blue stain fungi and wood rot could be efficiently prevented with the composition of the invention. Further, it also acts as insect pest repellent, and considerably improves fire resistance of wood. Moreover, dimensional changes and cracking of wood during storage and long term use could be prevented with the composition, said composition also contributing to the preservation of the original colour of the treated materials. Aqueous solutions of the salts of the invention are slightly acidic, neutral, or alkaline, said neutrality being advantageous for the treatment of wood. In addition, the composition of the invention was found to stay in wood without being substantially washed out.

DETAILED DESCRIPTION OF THE INVENTION

In this context, the term wood or wood material refers to all materials and products comprising wood, including raw timber, sawn timber, wooden construction materials and elements and wood-plastic composite products, and further, various processed wood products such as round logs, all sawn timber such as boards, planks, laths, flat elements such as laminates, for example chipboard, plywood or LVL products (Laminated Veneer Lumber), panels, slabs, wall elements and the like, furniture for indoors and outdoors, and other wooden articles and objects. The wood to be treated may also be present in immobile structures, particularly outdoors, such as wooden buildings, fences, framings, pillars, bridges, piers, etc.

The term chelating agent refers to agents that are able to bind, and form complexes with metal ions such as sequestering agents and chelates mentioned for instance in EP 1070045. Especially, the chelating agent according to the invention refers to chelating agents being able to bind metals of the transition groups of the periodic table of elements in addition to being able to bind alkali earth metal ions. Preferably the chelating agent according to the invention is a chelating agent being able to bind iron and manganese ions. The ability of the chelating agents to bind metal ions can be estimated by the values of the stability complexes, log K values, of the metal complexes (Martell, A. E., Smith, R. M., Critical Stability constants Database, NIST, Caitensburg, Md., USA, December 2003).

Most preferably a chelating agent according to the invention has the stability constant (log K value) for the iron complex over 12 and for the manganese complex the value is over 7.

The expression substantially biodegradable refers to biological degradability characteristic of some chelating compounds and salts thereof, such as ethylenediaminesuccinic acid (EDDS), iminodisuccinic acid (USA), N-bis-[2-(1,2-dicarboxyethoxy)-ethyl]-aspartic acid (AES). In addition to the monomeric compounds mentioned, biodegradable compounds include such naturally degradable polymeric compounds as poly-$\alpha$-hydroxyacrylic acid (PHAS), polyaspartamic acid (PASP), polylactic acid (PLA), and metal salts and derivatives thereof, and the like. In contrast to above compounds, poorly biodegradable chelating agents include e.g. ethylenediaminetetraacetic acid (EDTA), diethylenetriaminepentaacetic acid (DTPA), or the like as described in the patent FI106258.

The composition of the invention for the treatment of wood comprises at least one $C_1$-$C_7$-monocarboxylic acid or a salt, or mixtures thereof. The composition further comprises at least one chelating agent. These compounds dissolved in a liquid aqueous vehicle constitute the composition of the invention for the treatment of wood.

The chelating agent is preferably biodegradable or substantially biodegradable. The chelating agent, or agents in case it is necessary to use several chelating agents simultaneously, is/are selected from the group consisting of N-bis-[2-(1,2-dicarboxyethoxy)-ethyl]-amine derivative having the formula (1)

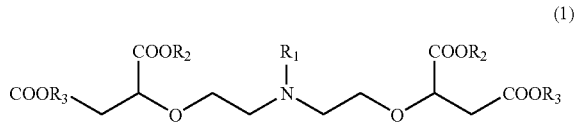

(1)

where $R_1$ represents an alkyl group, or a group having one or more carboxylic acid group(s) in the alkyl chain, hydroxylic group, or an ether bond, and $R_2$ and $R_3$ represent hydrogen, or an alkali metal or alkaline earth metal ion;
an aspartic acid derivative having a structure differing from that of the formula 1;
a polymer binding metals;
an organic phosphorus compound and a derivative thereof; and mixtures thereof.

The environmental load due to these compounds is as low as possible, and thus an aspartic acid derivative having a structure differing from that of the formula 1, and being biodegradable is preferable, the polymer binding metals being also biodegradable.

N-bis-[2-(1,2-dicarboxyethoxy)-ethyl]-amine derivatives of the invention, having the formula (I), preferably include N-bis-[2-(1,2-dicarboxyethoxy)-ethyl]-aspartic acid (AES), N-bis-[2-(1,2-dicarboxyethoxy)-ethyl]-glycine (GES), and N-bis-[2-(1,2-dicarboxyethoxy)-ethyl]-methylglycine (MGES). The N-bis-[2-(1,2-dicarboxy-ethoxy)-ethyl]-amine derivative is more preferably AES, a derivative such as a salt thereof, or a mixture of these compounds. The biodegradable aspartic acid derivative of the invention, having a structure different from that represented by the formula (I), is preferably the ethylenediaminesuccinic acid (EDDS), or iminodisuccinic acid (USA), or a derivative thereof. The biodegradable polymer of the invention that binds metals is preferably the polyaspartamic acid (PASP), polylactic acid (PLA), poly-α-hydroxyacrylic acid (PHAS), or a salt thereof being sufficiently biodegradable and causing no substantial environmental load. An advantage of amine derivatives is further the fact that there is no phosphorus in the structure, and thus the potential nutrient load is not increased. It was found that organic phosphorus compounds are also able to function in a comparable manner with the above compounds. The organic compound is preferably an organic phosphonic acid. More preferably, the organic phosphonic acid is diphosphonic acid, triphosphonic acid or tetraphosphonic acid, or pentaphosphonic acid or a salt or mixture thereof. Especially preferred phosphonic compounds are aminotrimethylenephosphonium acid (ATMP), 1-hydroxyethylid ene-1,1-diphosphonic acid (HEDP), ethyl enediaminetetramethyl-enephosphonic acid (EDTMP), or diethylenetriaminepantamethylenephosphonic acid (DTPMP), or a salt or mixture thereof. Most preferably, the organic phosphorus compound is HEDP, a salt or a mixture thereof. Yet, most preferably, the chelating agent of the invention comprises AES, or a salt thereof and/or HEDP or a salt thereof. These compounds are excellent agents for the improvement of the biological protection, and fire resistance of wood, and they cause only minor environmental loads.

The total amount of the chelating agent in the composition of the invention varies from 0.01 to 50%, preferably from 0.5 to 20% by weight. More dilute solutions are used in case of pressurized impregnation, while compositions having higher conentrations are used for surface treatments.

According to a preferable embodiment where fire protection is prioritized, an organic phosphorus compound, preferably HEDP, is used as the chelating agent in an amount of 5 to 20% by weight.

According to another embodiment where biological protection is prioritized, N-bis-[2-(1,2-dicarboxyethoxy)-ethyl]-amine derivatives, preferably AES, is used in an amount of 0.5 to 5%, by weight.

In the composition of the invention, one or several different chelating agent(s) such as AES and HEDP may be used simultaneously.

The $C_1$-$C_7$ monocarboxylic acid is preferably selected from the group consisting of formic acid, acetic acid, propionic acid, sorbic acid, benzoic acid, and mixtures thereof. Said acids and salts thereof are readily commercially available, and common in food industry, and as is known, the antibacterial properties thereof are the best among salts of organic acids. The $C_1$-$C_7$ monocarboxylic acid of the invention is preferably formic acid or sorbic acid, or a mixture thereof, said acids having a very good antibacterial activity. The $C_1$-$C_7$ monocarboxylic acid is most preferably formic acid or a salt thereof, which act as an excellent wood protecting agent in combination with the chelating agent of the invention, and has the above advantages, and competitive working costs.

The salt of the $C_1$-$C_7$ monocarboxylic acid is preferably an alkali, or alkaline earth metal salt, or an ammonium salt, or a mixture thereof. If necessary, the salt may also be produced in or ex situ by neutralizing the respective suitable compound to form a salt thereof. For instance an ammonium salt may be produced by neutralizing an acid to form a salt. The cation of the salt is preferably sodium, potassium, magnesium, calcium and/or ammonium, or a mixture thereof. The anion of the salt is preferably a formate and/or sorbate having superior antibacterial activity and being sufficiently soluble in water. Most preferably the salt is a potassium, calcium or ammonium salt of formate, or a mixture thereof.

According to a preferable embodiment, in case rot protection property is particularly prioritized, the salt of the $C_1$-$C_7$ monocarboxylic acid is calcium formate, which excellently acts as a wood protecting agent in combination with a chelating agent of the invention particularly for rot prevention, especially in case of pressurized impregnation. Moreover, handling properties of calcium formate are agreeable. Low hygroscopicity is an advantage of calcium formate.

According to another preferable embodiment, in case fire protection property is particularly prioritized, the salt of the $C_1$-$C_7$ monocarboxylic acid is ammonium formate having a very high solubility in water, and thus no additional metal cations to be chelated are entrained into the composition. During the production of ammonium formate preferably carried out in situ, the chelating agent may at the same time be ammonated to give the corresponding ammonium salt. An ammonium salt may also be used in chelate solutions, which are preferably concentrated.

Further, according to a preferable embodiment, in case protection against termite attacks is prioritized, the salt of the $C_1$-$C_7$ monocarboxylic acid is potassium formate. Preferably a concentrated composition comprising formate may be applied with a brush on the surface to be treated. The concentration of the solution reduces the necessary volume and need for storage, as well as transportation costs.

The composition according to the invention comprises 1 to 70% by weight of the $C_1$-$C_7$ monocarboxylic acid or a salt thereof. Preferably, the amount of the monocarboxylic acid or a salt thereof varies between 1 and 50% by weight. The amount is preferably 1 to 20%, by weight. The amount is calculated on the basis of the total amount of all $C_1$-$C_7$ monocarboxylic acids or salts thereof present in the composition.

One preferable embodiment comprises 2 to 30%, by weight of the $C_1$-$C_7$ monocarboxylic acid or a salt thereof, said amount giving a sufficient retention, and amount of the agent in wood, and being able to provide a sufficient prolonged protection against organisms decaying wood.

The pH of the composition of the invention is between 2 and 12, preferably between 4 and 10, more preferably between about 4 and 7, as measured directly from the solution. For instance any additives used such as alkyl ketene dimer AKD require pH values close to 5 to remain dissolved in the solution and to keep the composition sufficiently stable. On the other hand, wood structure is readily damaged with time by highly acidic agents used for wood protection, or for fire resistance. They also cause harm to metallic construction materials such as nails, or screws in wood thus treated due to liability of metals to rust.

The components of the composition of the invention may be dissolved in an aqueous vehicle. Thus a fluid composition is obtained that may be at least partly delivered into wood by several methods. If necessary, the fluidity of the composition may be adjusted with additives known in the art, such as carboxymethyl cellulose (CMC). The composition of the invention is preferably in a concentrated form, for instance for transportation and storage, and may be suitably diluted for the application, said dilution being preferably carried out at the site of use prior to contacting the wood with the composition.

According to a particular embodiment, the composition of the invention for the treatment of wood comprises 5 to 20% of HEDP, and 1.0 to 10%, by weight, of the $C_1$-$C_7$ monocarboxylic acid, or a salt thereof, preferably ammonium formate, and water.

Further, retention agents and/or hydrofobizing agents may be added to the composition of the invention. Suitable retention agents may be fatty acids, polymers such as starch, cellulose or derivatives thereof, chitosan, poorly soluble formates or silicon compounds. Hydrophobizing agents include resins and derivatives thereof, surface sizes such as alkyl ketene dimer (AKD) or alkenylsuccinic acid (ASA), and tall oil and the derivatives thereof AKD, ASA and/or tall oil are preferably used as hydrofobizing agents, the preferable amount thereof being 0.01 to 5.0% by weight. In addition to the provision of rot and mould inhibition, a particular advantage of the composition is the fact that it significantly improves the fire resistance of wood. The addition of AKD, ASA, or tall oil further prevents the chelating agent or the salt thereof, and/or monocarboxylic acid or the salt thereof from being washed out of wood.

According to another particularly preferable embodiment, the composition of the invention comprises 0.1 to 5% of AES, and 1 to 5%, by weight, of a $C_1$-$C_7$ monocarboxylic acid or a salt thereof, e.g. calcium formate, and water. Moreover, 0.01 to 5.0% by weight of AKD or ASA may be added to the composition to further improve the water-repellency of the wood.

Also an organic biocide, such as iodopropan-2-yl-N-butyl-carbamate (IPBC), polyhexamethylene guanidinium (PHMG) compounds such as chloride or sulfate salts thereof, propiconazole, or the like may be added to the composition of the invention. The organic biocide is preferably IPBC, PHMG and/or propiconazole. Said organic biocide is preferably used in an amount of 0.01 to 5.0%, more preferably 0.01 to 1.0%, by weight, to further reduce growth of moulds and blue stain fungi. A product resistant to long term exposition to moulds (standard EN 130) is thus obtained.

According to the application, the composition of the invention may contain different additives. In case the agent is used for surface treatment, dyes such as organic dyes preferably in an amount of 1 to 85% by weight, or pigments preferably in an amount of 1 to 85% by weight may be added thereto to also visually modify the treated wooden surface as with painting. CMC may serve as a bonding agent, which also acts as a rheological adjuvant. The pigments and organic dyes used are preferably free of heavy metals. For instance known iron oxide pigments may be used as pigments.

Physical properties of the compositions to be applied on surfaces with brushes may also be selected according to the application purpose, that is, the viscosity thereof may be higher than that of a composition for impregnation since a composition for impregnation should readily penetrate into the wood. It should, however, be noted that some penetration (in millimeter range) of active agents into wood occurs even with compositions to be applied with a brush, also with viscous compositions.

Also a method according as described herein for the treatment of wood is disclosed in the invention wherein wood and a composition comprising at least one $C_1$-$C_7$ monocarboxylic acid or a salt thereof or mixtures thereof, and at least one chelating agent dissolved in a liquid aqueous vehicle are contacted with one another.

The discussion presented for the composition of the invention applies to said $C_1$-$C_7$ monocarboxylic acid, the salts thereof, and chelating agents.

Prior to the treatment of wood, the treatment composition may be diluted with water to give the concentration suitable for the treatment.

The composition may be absorbed to the wood to be treated over the whole thickness thereof, or to a certain depth from the surface, for instance by impregnation, immersion, spraying, vaporization (nebulization), or by application with a brush. Since various alternatives exist, the treatment may be carried out during other processing of wood at a suitable point, for instance during the final drying of wood. Physical properties of the composition such as viscosity may be adjusted according to the type and purpose of the treatment.

The composition of the invention may be heated and/or an elevated temperature may be used in the process, thus further improving the absorption. Absorption is also improved by sub- and superatmospheric pressures as is known for conventional CCA impregnation. In general, the composition of the invention may be used by the same procedures commonly used to impregnate wood, such as pressurized impregnation. The fact that the composition is environmentally friendly offers, however, many other possibilities for use in wood construction and indoor building applications that may not have been carried out with more toxic agents.

The method of the invention is particularly applicable to treatment processes where efficient penetration even up to the wood core is necessary, such as impregnation. The agent may be forcibly made to penetrate into the wood for instance by a common pressurized impregnation process wherein wood is first subjected to vacuum for water removal, followed by contacting the agent with wood and promoting the penetration thereof into wood by using elevated pressures.

The invention enables a convenient procedure for the treatment of wood materials in a cost effective manner, said procedure being easily incorporated into other common processes as one stage in the process line comprising successive steps for the treatment of wood products or articles. An aspect of the composition of the invention is also pleasant handling since no irritating odors are released.

The composition of the invention is suitable for the treatment of both processed and raw wood and may be performed either at the site of storage of wood or separately in a treatment plant for wood products where the contact between the treatment agent and wood may be achieved in several ways. The invention is also suitable for the protection of finished immobile constructions, particularly outdoors, such as outdoor furniture, piers, bridges, pillars, and buildings mainly by spraying or application with a brush. Being safe, the agent may be used for treatment of finished wooden constructions at the site of use without any special precautions.

The method of the invention is also suitable for products consisting not only of wood but of a combination of wood and another material. The requirement is that the treatment is directed to the wooden parts of the products.

Wood treated with the above treatment agent as described herein is also disclosed in the invention, said wood comprising due to the treatment at least one $C_1$-$C_7$ monocarboxylic acid or a salt or mixtures thereof, and further, at least one chelating agent in addition to wood material.

It is contemplated that the performance of treatment composition of the invention is based on the modification of wood by the carboxylic acid or the corresponding carboxylate in combination with the chelating agent without binding thereto. The protection for instance against rot organisms, fire, blue stain and/or colour changes provided by carboxylic acids or derivatives thereof, or the chelating agents used alone is not as superior and efficient as that provided by combinations thereof in the same composition.

According to the present disclosure, the treatment agent for wood may be used for the protection of wood against one, or simultaneously against several detrimental environmental factors. Said factors mainly include mould, rot, blue stain, insect such as termites attacks on wood, fire hazard, color changes, dimensional changes, or a combination thereof due to environmental influence.

The composition may be tailored to correspond with the respective protection needed and prioritized. Preferably, a composition simultaneously having sufficient activities against several different detrimental environmental influences is provided.

According to a preferable embodiment, a treatment agent of the invention comprising 0.1 to 20% of AES, and/or 0.1 to 20% of HEDP, and 1 to 10% of a formate salt, by weight, are used to simultaneously provide both fire and rot protection.

According to another preferable embodiment, a treatment agent of the invention comprising 0.1 to 20% of AES, and/or 0.1 to 20% of HEDP, 1 to 10% of a formate salt, and 0.1-5% of AKD, by weight, are used to simultaneously provide protections against both fire, rot, dimensional changes and/or color changes.

Further, according to still another preferable embodiment, a treatment agent of the invention comprising 0.1 to 20% of AES, and/or 0.1 to 20% of HEDP, 1 to 10% of a formate salt, 0.1-5% of AKD, and 0.01 to 1.0% of IPBC, by weight, are used to simultaneously provide protections against both mould, fire, and rot, and prevention or delay of color changes of wood.

The invention is now described in more detail by examples. The purpose of the examples is to illustrate the invention, not to limit the scope thereof.

EXAMPLE 1

Rot Prevention Testing with the Wood Protecting Agent of the Invention

Biological resistance provided by the wood protecting composition was studied as follows:
Test material: pine
Wood protecting agent (samples):
1) Untreated pine (blank test, control)
2) Solution 1 (comparative solution, solution 1)
    100 g/kg of calcium formate+water
3) Solution 2 (solution according to the invention, solution 2)
    30 g/kg of calcium formate+10 g/kg of AES+7.5 g/kg of AKD+water Impregnations of the test samples were carried out according to the laboratory procedure described in the standard EN 113. The procedure comprised the following steps: an absolute pressure of 7 mbar was provided in a chamber by evacuation with a vacuum pump. A vessel containing the test samples was placed in the chamber prior to evacuation. The absolute 7 mbar pressure was maintained for 15 minutes. The impregnation agent was introduced into the vessel containing the test samples, present in the chamber, by opening the valve. The impregnation agent was sucked into the vessel by the vacuum. The pressure was released immediately after filling of the vessel. The test samples remained in the impregnation agent for two hours. The impregnation agent was added to the vessel according to the absorption of the agent into wood.

Mean penetration of the comparative solution (solution 1) during the impregnation was 762.9 kg/m$^3$. The amount of calcium formate penetrated into the wood was 65.7 kg/m$^3$, calculated on the basis of the mean, and a 10% solution.

Mean penetration of the inventive solution (solution 2) during the impregnation was 696.8 kg/m$^3$. The amount of calcium formate penetrated into the wood was 20.9 kg/m$^3$, while that of the chelating agent (AES) was 6.9 kg/m$^3$, calculated on the basis of the mean, and a 3% solution, suggesting that the solution of the invention is a very economical and competitive wood protecting agent in comparison to the control solution.

Rot testing was carried out according to the EN 113 standard. 10 test samples impregnated with respective agents for each of the three rot fungi were used in the test. A sample made of surface wood of pine was placed as a control with the impregnated test samples to the same container for the rot test. Activity of each fungus was tested with eight test samples (so-called infection test). Said test samples for the fungus activity testing were placed in respective containers for the rot test without impregnated test samples.

Following fungi were used in the testing:

1) *Coniophora puteana*

2) *Gloeophyllum trabeum*

3) *Oligoporus placenta*

Rot resistance classes were determined according to the EN 350-1 standard from the results of the rot testing. In the method, an X value was calculated for each impregnation batch and for each fungus, said X value describing the ratio of the mass loss of the impregnated test samples to that of the unimpregnated control samples. X value was calculated by dividing the corrected mass loss of the impregnated test samples by that of the unimpregnated control samples. The calculation was based on mean values. Based on the result obtained, the rot resistance class was determined as follows for the fungus with the highest rot activity:

Class 1=extremely resistant $X \leq 0.15$

Class 2=resistant $0.15 < X \leq 0.30$

Class 3=reasonably resistant $0.30 < X \leq 0.60$

Class 4=somewhat resistant $0.60 < X \leq 0.90$

Class 5=non-resistant $X > 0.90$

Rot resistance classes and mean mass losses of pine samples impregnated with the control solution (solution 1) and solution of the invention (solution 2) are shown in the table 1.

TABLE 1

Rot resistance classes and mean mass losses

|  | Mass loss (comparison), % | Class |
|---|---|---|
| *Oligoporus placenta* | | |
| Solution 1: 10% calcium formate | 19.42 (38.94) | 3 |
| Solution 2: 3% of calcium formate + AKD + AES | 0 (32.53) | 1 |
| *Gloeophyllum trabeum* | | |
| Solution 1: 10% calcium formate | 22.06 (45.61) | 3 |
| Solution 2: 3% of calcium formate + AKD + AES | 1.29 (41.08) | 1 |
| *Coniophora puteana* | | |
| Solution 1: 10% calcium formate | 15.94 (38.18) | 3 |
| Solution 2: 3% of calcium formate + AKD + AES | 0.23 (41.40) | 1 |

Lower penetration depth, yet a better final result in the rot resistance testing were obtained with a composition of the invention containing a substantially lower amount of calcium formate.

Due to lower penetration of water in comparison to the solution 1, lower mass loss was caused by the 3% calcium formate solution tested in a similar manner, comprising AKD but no chelating agent, however, without any substantial improvement of the rot resistance classification. A weight loss result similar to that obtained with the solution 2 was produced by a solution containing only AES without calcium formate.

EXAMPLE 2

Fire Resistance Testing with the Wood Protecting Agent of the Invention

Test material: pine
Wood protecting agents (samples):
1) Solution 3 (control solution 2)
   120 g/kg of potassium formate+120 g/kg of potassium sorbate+water
2) Solution 4 (solution of the invention)
   78 g/kg of formic acid+390 g/kg of HEDP+water
   the pH of the solution was adjusted to the value of 6, thus resulting in the composition of about 100 g/kg of ammonium formate+200 g/kg of ammonized salt of HEDP.

Penetrated amount of the control solution 2 (solution 3) during the impregnation was about 759 kg/m$^3$. The amounts of potassium formate, and potassium sorbate penetrated into the wood were 90 kg/m$^3$ 90 kg/m$^3$, respectively, calculated for a 12% solution. The total amount of these two salts penetrated into the wood was 180 kg/m$^3$.

Penetrated amount of the solution of the invention (solution 4) during the impregnation was 743.2 kg/m$^3$, resulting in the total penetrated amount of the fire prevention agent the total concentration effective agent is 22.7% for wood of 176.2 kg/m$^3$.

It was found that the quality of the carboxylate salt played no role for fire prevention. Sorbate is only less inflammable than formate. In addition, the inflammability of wood treated with ammonium formate is comparable to that of wood treated with potassium formate.

Fire resistance of the impregnated test samples was evaluated according to the ISO 5660-1:2002 test using a conical calorimeter.

For the control solution 2 (solution 3), the ignition time was 17 seconds, the $1^{st}$ maximum of the heat production rate being 200 kW/m$^2$, whereas for the agent of the invention (solution 4), the ignition of impregnated test samples failed, the $1^{st}$ maximum of the heat production rate being only 10 kW/m$^2$.

EXAMPLE 3

Testing Against Blue Stain Formation with the Wood Protecting Agent of the Invention Testing of blue stain formation was carried out according to the modifies EN 152.2 standard for the solutions 1 (control solution 1), 2 (solution according to the invention), 3 (control solution 2), and 4 (solution according to the invention). Untreated pine surface wood served as the blank in the test. The number of test samples was 8/batch.

For the test, two different blue stain fungi were grown, and pooled after being grown for more than three weeks to obtain one suspension. The fungi used were:
1) *Aureobasidium pullulans*
2) *Sclerophoma pithyophila*.

The test samples and the test flasks of the blue stain fungi were sterilized by irradiation, and with vapor, respectively. After sterilization, the test samples were dipped into the sterile fungal suspension and placed into flasks. Finally, fungal suspension was poured on the test samples. The flasks were placed to a conditioned chamber (relative humidity RH 70%, temperature +22° C.).

This blue stain test was monitored for 20 weeks. The results of this blue stain test are based on visual evaluations. Blue stain formation in the test samples is evaluated on the scale 0 to 5:
1. pure (less than 5% of the surface of the test sample covered by microbial growth)
2. low amounts of microbial growth (about 5 to 20% of the surface of the test sample covered by microbial growth)
3. moderate amounts of microbial growth (about 20 to 40% of the surface of the test sample covered by microbial growth)
4. high amounts of microbial growth (more than 40% of the surface of the test sample covered by microbial growth)
5. extreme amounts of microbial growth (90 to 100% of the surface of the test sample covered by microbial growth).

| Treatment solution | Microbial growth 0 to 5 |
|---|---|
| Blank (untreated pine) | 5 |
| Solution 1: 100 g/kg of calcium formate + water | 4 |
| Solution 2: 30 g/kg of calcium formate + 10 g/kg of AES + 7.5 g/kg of AKD + water | 1 |
| Solution 3: 120 g/kg of potassium formate + 120 g/kg of potassium sorbate + water | 3 |
| Solution 4: 78 g/kg of formic acid + 390 g/kg of HEDP + water | 1 |
| Literature reference: 1.0% of NHA* | 4 |

*Green et al; International Biodeterioration & Biodegradation, vol. 39. No. 2-3 (1997) 103-111. NHA refers to a chelating agent called N,N-naphthaloylhydroxylamine.

The solutions 2 and 4 of the invention significantly inhibited the growth of blue stain fungi on wood surface in comparison to a formate solution, or a chelate solution alone.

EXAMPLE 4

Effect of the Wood Protecting Agent of the Invention on Mechanical Properties of Sawn Timber The effect of the solution of the invention (solution 4 of the example 2) on the strength and mechanical properties of wood were assayed in the flexural test for sawn timber (pine) treated with the agent, after being subjected to external heat and moisture stress (condition 1: temperature +60° C., RH 50%, testing time 3.5 months), and conditioning (condition 2: temperature +20° C., RH 65%).

Under moisture and heat stress, the flexural strength was increased by the agent of the invention from 41.1 N/mm$^2$ to 68.7 N/mm$^2$ (condition 1), and to 84.4 N/mm$^2$ (condition 2).

Under moisture and heat stress, the elastic modulus was increased by the agent of the invention from 5847 N/mm$^2$ to 14700 N/mm$^2$ (condition 1), and to 15490 N/mm$^2$ (condition 2).

Flexural strength of untreated sawn timber was increased from 45.8 N/mm$^2$ to 75.3 N/mm$^3$ (condition 1). Elastic modulus of untreated sawn timber was increased from 6257 N/mm$^2$ to 14800 N/mm$^3$ (condition 1).

Both the flexural strength and elastic modulus of sawn timber treated with the solution of the invention (solution 4) were slightly decreased. Under moisture and heat stress, both the flexural strength and elastic modulus were somewhat increased.

The results show that impregnation using even such high chemical loads under external humidity and temperature had no significantly detrimental effect on mechanical properties of treated wood.

EXAMPLE 5

Retention of the Wood Treating Agent of the Invention, and Effect Thereof on Cracking and Darkening of Sawn Timber Only about one fifth of the agent of the invention (solution 4) was washed out of the wood after being subjected to external heat and humidity stress (condition 1: temperature +60° C., humidity RH 50%, testing time 3.5 months). In contrast, amounts washed out of wood treated only with a chelating agent such as EDTA were so high that it was necessary to add for instance siloxan compounds or fluoroalkyl polymers to the treatment to reduce the amounts washed out as described in WO 0123154. About one third of a fire protection agent based on commercial borax was washed out in a similar test.

Accordingly, the rate of washing out of the wood treatment agent of the invention is reasonably low in comparison to other rot or fire prevention agents.

EXAMPLE 6

Effect of the Wood Treatment Agent of the Invention on Cracking and Darkening of Sawn Timber Dimensional stability and colour fastness of sawn timber impregnated with solutions of the invention (solutions 2 and 4) were also tested and evaluated by visual inspection. No cracking was found in wood treated with the treatment solution in comparison to the original wood material. Darkening of the surface of the treated wood was also not observed in comparison to the original wood material, at least not during the one year monitoring period of the test results. Untreated control sample clearly cracked and darkened.

EXAMPLE 7

Effect of the Wood Protecting Agent of the Invention on the Termite Resistance of Sawn Timber Performance of the treatment solution with respect to termite resistance was tested by completely introducing sawn timber treated with solutions 2 and 4 into a termite nest for three months. No destruction by termites was found for the treated sawn timber compared to the untreated control sample, that is, original sawn timber.

The invention claimed is:

1. A method for the treatment of wood, comprising contacting wood with a composition comprising at least one $C_1$-$C_7$-monocarboxylic acid or a salt or a mixture thereof, and at least one chelating agent selected from the group consisting of N-bis-[2-(1,2-dicarboxyethoxy)-ethyl]-aspartic acid (AES), N-bis-[2-(1,2-dicarboxyethoxy)-ethyl]-glycine (GES), N-bis-[2-(1,2-dicarboxyethoxy)-ethyl]-methylglycine (MGES), ethylenediaminesuccinic acid (EDDS), iminodisuccinic acid (ISA), polyaspartamic acid (PASP), polylactic acid (PLA), poly-α-hydroxyacrylic acid (PHAS), and a derivative and a mixture thereof, dissolved in a liquid aqueous vehicle.

2. The method according to claim 1, further comprising diluting a concentrated composition with water to give said composition for contacting said wood.

3. A treated wood prepared by the method according to claim 1, and comprising at least one $C_1$-$C_7$-monocarboxylic acid or a salt or a mixture thereof, and at least one chelating agent selected from the croup consisting of N-bis-[2-(1,2-dicarboxyethoxy)-ethyl]-aspartic acid (AES), N-bis-[2-(1,2-dicarboxyethoxy)-ethyl]-glycine (GES), N-bis-[2-(1,2-dicarboxyethoxy)-ethyl]-methylglycine (MGES), ethylenediaminesuccinic acid (EDDS), iminodisuccinic acid (USA), polyaspartamic acid (PASP), polylactic acid (PLA), poly-α-hydroxyacrylic acid (PHAS), and a derivative and a mixture thereof.

4. A composition for treating wood, comprising
i) propionic acid or sorbic acid or a salt thereof; calcium formate; or a mixture thereof, and
ii) a chelating agent selected from the group consisting of N-bis-[2-(1,2-dicarboxyethoxy)-ethyl]-aspartic acid (AES), N-bis-[2-(1,2-dicarboxyethoxy)-ethyl]-glycine (GES), N-bis-[2-(1,2-dicarboxyethoxy)-ethyl]-methylglycine (MGES), ethylenediaminesuccinic acid (EDDS), iminodisuccinic acid (ISA), polyaspartamic acid (PASP), polylactic acid (PLA), poly-α-hydroxyacrylic acid (PHAS), and a derivative and a mixture thereof.

5. A composition for treating wood, comprising
i) at least one $C_1$-$C_7$ monocarboxylic acid or a salt or a mixture thereof, and
ii) a chelating agent selected from the group consisting of N-bis-[2-(1,2-dicarboxyethoxy)-ethyl]-aspartic acid (AES), N-bis-[2-(1,2-dicarboxyethoxy)-ethyl]-glycine (GES), N-bis-[2-(1,2-dicarboxyethoxy)-ethyl]-methylglycine (MGES), ethylenediaminesuccinic acid (EDDS), iminodisuccinic acid (ISA), polyaspartamic acid (PASP), polylactic acid (PLA), poly-α-hydroxyacrylic acid (PHAS), and a derivative and a mixture thereof.

6. The composition according to claim 5 wherein the pH of said composition is between 4 and 7.

7. The composition according to claim 5, wherein said $C_1$-$C_7$ monocarboxylic acid is formic acid, sorbic acid, or a mixture thereof.

8. The composition according to claim 5, comprising said salt of at least one $C_1$-$C_7$ monocarboxylic acid; wherein said salt is an alkali or alkaline earth metal salt, or an ammonium salt.

9. The composition according to claim 8, wherein said salt is a calcium salt or the ammonium salt.

10. The composition according to claim 5, comprising said salt of at least one $C_1$-$C_7$ monocarboxylic acid; wherein the $C_1$-$C_7$ monocarboxylic acid salt is calcium formate or ammonium formate.

11. The method according to claim 1, wherein the chelating agent comprises N-bis-[2-(1,2-dicarboxyethoxy)-ethyl]-aspartic acid (AES) or a salt thereof; and wherein the $C_1$-$C_7$ monocarboxylic acid or a salt or a mixture thereof comprises sorbic acid or a salt thereof, calcium formate or ammonium formate.

12. The treated wood according to claim 3, wherein the chelating agent comprises N-bis-[2-(1,2-dicarboxyethoxy)-ethyl]-aspartic acid (AES) or a salt thereof; and wherein the $C_1$-$C_7$ monocarboxylic acid or a salt or a mixture thereof comprises sorbic acid or a salt thereof, calcium formate or ammonium formate.

13. The composition according to claim 4 wherein the pH of said composition is between 4 and 7.

14. The composition according to claim 4, wherein said $C_1$-$C_7$ monocarboxylic acid is formic acid, sorbic acid, or a mixture thereof.

15. The composition according to claim 4, comprising said salt of at least one $C_1$-$C_7$ monocarboxylic acid; wherein said salt is an alkali or alkaline earth metal salt, or an ammonium salt.

16. The composition according to claim 15, wherein said salt is a calcium salt or the ammonium salt.

17. The composition according to claim 4, comprising said salt of at least one $C_1$-$C_7$ monocarboxylic acid; wherein the $C_1$-$C_7$ monocarboxylic acid salt is calcium formate or ammonium formate.

* * * * *

UNITED STATES PATENT AND TRADEMARK OFFICE
CERTIFICATE OF CORRECTION

PATENT NO. : 8,399,106 B2
APPLICATION NO. : 12/745584
DATED : March 19, 2013
INVENTOR(S) : Kukkonen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 314 days.

Signed and Sealed this
First Day of September, 2015

Michelle K. Lee
*Director of the United States Patent and Trademark Office*